United States Patent
Patel et al.

(10) Patent No.: US 11,911,233 B2
(45) Date of Patent: Feb. 27, 2024

(54) DRILL FOR SURGICAL SCREW INSERTION WITH REORIENTED TORQUE

(71) Applicants: Amit R. Patel, Lutherville-Timonium, MD (US); A. Frederick Hess, Oviedo, FL (US)

(72) Inventors: Amit R. Patel, Lutherville-Timonium, MD (US); A. Frederick Hess, Oviedo, FL (US)

(*) Notice: Subject to any disclaimer, the term of this patent is extended or adjusted under 35 U.S.C. 154(b) by 433 days.

(21) Appl. No.: 17/183,944

(22) Filed: Feb. 24, 2021

(65) Prior Publication Data
US 2021/0259803 A1    Aug. 26, 2021

Related U.S. Application Data

(60) Provisional application No. 62/981,490, filed on Feb. 25, 2020.

(51) Int. Cl.
*A61C 3/02* (2006.01)
*A61F 2/46* (2006.01)
(Continued)

(52) U.S. Cl.
CPC ............ *A61C 3/02* (2013.01); *A61B 17/1624* (2013.01); *A61B 17/7082* (2013.01); *A61B 17/8875* (2013.01); *A61F 2/4611* (2013.01)

(58) Field of Classification Search
CPC ... A61C 3/02; A61B 17/1624; A61B 17/7082; A61B 17/16; A61B 17/8875; A61B 17/1631; A61B 17/1622; A61F 2/4611
(Continued)

(56) References Cited

U.S. PATENT DOCUMENTS 2,138,862 A * 12/1938 Johnston ................ B23D 51/16
                                                                 74/44
2,439,803 A *  4/1948 Giesen ............... A61B 17/1622
                                                                 81/34
(Continued)

FOREIGN PATENT DOCUMENTS

CN    110974342    12/2019
CN    211633467    10/2020
(Continued)

OTHER PUBLICATIONS

"Right Angle Drill Adapter Flexible Shaft Extension Bits & Screwdriver Hold ¼", available at https://www.ebay.com/itm/Right-Angle-Drill-Adapter-Flexible-Shaft-Extension-Bits-Screwdriver-Hold-1-4/293457178267 (checked Feb. 14, 2021). See also U.S. Pat. No. 7,191,677 B2, issued Mar. 20, 2007; and U.S. Pat. No. 2,707,233, issued Apr. 24, 2007.

(Continued)

*Primary Examiner* — Jessica Weiss
(74) *Attorney, Agent, or Firm* — FRESH IP PLC; Andrew Berks (57) ABSTRACT

An instrument is provided for rotatably driving a screw or drill bit into bone in surgery, comprising a gear housing at a distal end of a drive shaft, wherein the drive shaft has a proximal end adapted for connection to a rotational power source, wherein the gear housing comprises at least one pair of bevel gears that direct the rotational force from the drive shaft in an approximately 115°-145° angle from the drive shaft to rotatably drive a screw or drill bit into bone during a surgical procedure. The device would advance or retract a drill or driver at a fixed angle in a manner that is user-friendly and ergonomic. The device addresses concerns with modern instrumentation that is cumbersome to use and does (Continued)

not allow the user generated forces to be efficiently applied to the intended trajectories.

8 Claims, 8 Drawing Sheets

(51) Int. Cl.
*A61B 17/16* (2006.01)
*A61B 17/70* (2006.01)
*A61B 17/88* (2006.01)

(58) Field of Classification Search
USPC .......................................... 606/80, 104, 99
See application file for complete search history.

(56) References Cited

U.S. PATENT DOCUMENTS

| | | | | |
|---|---|---|---|---|
| 3,120,845 A * | 2/1964 | Horner | ............... | A61B 17/1624 |
| | | | | 173/217 |
| 5,888,200 A * | 3/1999 | Walen | ................ | B25F 3/00 |
| | | | | 606/167 |
| 7,191,677 B2 | 3/2007 | Barkdoll | | |
| 7,207,233 B2 | 4/2007 | Wadge | | |
| 7,406,775 B2 * | 8/2008 | Funk | ................ | A61F 2/4405 |
| | | | | 606/97 |
| 9,022,888 B2 * | 5/2015 | McClung | ............... | B25B 21/026 |
| | | | | 475/149 |
| 9,470,297 B2 * | 10/2016 | Aranyi | ............... | A61B 17/0686 |
| 2002/0096389 A1 | 7/2002 | Saruwatari et al. | | |
| 2003/0225344 A1 * | 12/2003 | Miller | ................ | A61B 17/1671 |
| | | | | 600/568 |
| 2005/0171504 A1 * | 8/2005 | Miller | ................ | A61B 17/3476 |
| | | | | 604/506 |
| 2007/0282344 A1 * | 12/2007 | Yedlicka | ............ | A61B 17/1671 |
| | | | | 606/80 |
| 2014/0276891 A1 * | 9/2014 | Defalco | ............. | A61B 17/8894 |
| | | | | 606/104 |
| 2021/0030564 A1 | 2/2021 | Bae et al. | | |

FOREIGN PATENT DOCUMENTS

| | | |
|---|---|---|
| WO | 2015/057195 A1 | 4/2015 |
| WO | 2020/141408 A1 | 7/2020 |

OTHER PUBLICATIONS https://www.stryker.com/us/en/orthopaedic-instruments/products/system-8-cordless-driver-and-sabo.html, checked Feb. 20, 2021.
https://www.orthopedicdrills.com/product/nd-1011-dual-functional-electric-bone-drill, checked Feb. 20, 2021.

* cited by examiner

DRILL FOR SURGICAL SCREW INSERTION WITH REORIENTED TORQUE

CROSS REFERENCE TO RELATED APPLICATION(S)

This patent application claims priority to U.S. Patent Application 62/981,490, filed Feb. 25, 2020, the contents of which are incorporated by reference.

FIELD OF THE INVENTION

This invention pertains to an instrument for rotatably driving a screw or drill bit into bone in orthopedic surgery including a gear housing comprises at least one pair of bevel gears that direct a rotational force from a drive shaft in an approximately 115°-145° angle from the drive shaft.

BACKGROUND

Various types of interbody implants or cages are used in spinal surgery and other orthopedic surgical procedures for the purposes of decompression, stability, deformity correction, or fusion. These are placed in the intervertebral disc space after the disc material is removed. Once the implant or cage is placed in the desired location, typically some form of fixation is required the stabilize the construct. Traditionally, this has been some variation of plates or screws. Newer implants have screws that are integrated with the implant itself that eliminate the need for bulky plates and screws constructs.

Once a cage is in position, an angled or articulating drill is utilized to create a path for a screw to be inserted. Both the drill and the screw are placed at a roughly 35°-55° degrees (typically 45°) from the axis of the cage to allow for maximal fixation strength.

The difficulty with this technique is related to the limited space available and often tenuous or critical anatomical structures that impede ideal placement of the screws. Thus, given anatomical constraints, screws are rarely placed at the typical 45° (but in the range of 35°-55°) angle. Furthermore, all of the devices utilized to drill and place the screws are working in-line with the trajectory of the drill/screw whereas the majority of the axial load and torsional force is somewhat orthogonal to that ideal trajectory. This further complicates the ability to accurately place these integrated fixation screws.

Thus, the problem addressed in this invention is a means to rotatably insert screws or drill holes in bone that reorients the torque from a driver from a comfortable position for the surgeon which maximizes control over the orientation and pressure applied by the surgeon during the rotational insertion process, to the correct angle for maximal strength of the implant. Currently available angled or articulated drills are difficult or impossible to place in the proper orientation to insert screws or drill holes, and difficult to control precisely, which is critical in surgery. For example, various adapters and flexible extenders for redirecting rotational energy are known in the art,[1] but none provide the control desirable for surgery.

[1] See, e.g., "Right Angle Drill Adapter Flexible Shaft Extension Bits & Screwdriver Hold ¼", available at https://www.ebay.com/itm/Right-Angle-Drill-Adapter-Flexible-Shaft-Extension-Bits-Screwdriver-Hold-1-4/293457178267 (checked Feb. 14, 2021). See also U.S. Pat. No. 7,191,677 B2, issued Mar. 20, 2007; and U.S. Pat. No. 2,707,233, issued Apr. 24, 2007.

SUMMARY OF THE INVENTION

In order to address the above-mentioned concerns, this invention provides the ability to place a drill or screw at a fixed angle in a relatively smaller working corridor and in a simpler more natural position in relation to a surgeon, by reorienting the torque from a rotational power source. The invention, as described herein, is more user-friendly and ergonomic than prior art solutions to the problem of properly orienting screw or drill trajectories. This invention pertains to a device that is in-line or non-orthogonal with respect to the surgeon and allows for drilling or placement of a screw at a fixed angle for the purposes of securing a cage or instrumentation in surgery, such as spinal surgery. As of now, no drills for use in orthopedic surgery allows for this as all current devices either use articulating hinges (such as universal or U joints) or flexible springs to obtain the ideal angle of insertion. These prior art devices have shortcomings, including lack of control of pressure and lack of control over the angle of the insertion. The inventive device addresses concerns with modern instrumentation that is cumbersome to use and does not allow the user generated forces to be efficiently applied to the intended trajectories In an embodiment, an instrument is provided for rotatably driving a screw or drill bit into bone in surgery, comprising a gear housing at a distal end of a drive shaft, wherein the drive shaft has a proximal end adapted for connection to a rotational power source, wherein the gear housing comprises at least one pair of bevel gears that direct the rotational force from the drive shaft in an approximately 115°-145° angle from the drive shaft to rotatably drive a screw or drill bit into bone during a surgical procedure. The inventive instrument functions as a drill or screwdriver for orthopedic surgery.

In an embodiment, an instrument is provided for rotatably driving a screw or drill bit into bone in surgery, where the instrument may include a drive shaft having a rotational power source at a proximal end for applying a rotational force to the shaft and a gear housing at a distal end of the drive shaft. The distal end of the drive shaft may be connected to a first bevel gear supported in the gear housing, such that the larger diameter of the first bevel gear is in the proximal orientation, such that rotation of the drive shaft causes the first bevel gear to rotate. The first bevel gear may mesh with a second bevel gear having an axis of rotation at a 55°-55° angle to direct a torque from the second bevel gear at the 25°-55° angle along a first internal shaft. The internal shaft may terminate at a first spur gear which in turn may mesh with a second spur gear. The second spur gear may drive a second internal shaft that is coupled to a head that rotatably drives a surgical screw or drill at a 115°-145° angle from the drive shaft. The rotational power source may be an electric or pneumatic motor. Alternatively, the proximal end of the drive shaft may include a handle that is manually rotated by a surgeon to cause the drive shaft to rotate.

In an embodiment, an instrument is provided for rotatably driving a screw or drill bit into bone in surgery. The instrument may include a drive shaft having a rotational power source at a proximal end for applying a rotational force to the shaft and a gear housing at a distal end of the drive shaft. The distal end of the drive shaft may be connected to a first bevel gear supported in the gear housing, such that the larger diameter of the first bevel gear is in the proximal orientation, such that rotation of the drive shaft causes the first bevel gear to rotate. The first bevel gear may mesh with a second bevel gear having an axis of rotation at a 35°-55° angle with respect to the drive shaft to direct a torque from the second bevel gear at the 35°-55° angle along a first internal shaft. The first internal shaft may terminate at a first spur gear. The first spur gear may mesh with at least one additional second spur gear, such that rotation of the at least one additional second spur gear causes a lead screw to rotate. The lead screw may mesh with a drive stage housing containing a first drive gear, such that rotation of the lead screw causes the first drive gear to rotate. Rotation of the first drive gear may cause the drive stage housing to move longitudinally along the lead screw. A second drive gear in the drive stage housing may mesh with the first drive gear, such that rotation of the first drive gear causes the second drive gear to rotate. The second drive gear may be connected to a head that rotatably drives a surgical screw or drill bit at a 115°-145° angle from the drive shaft. The longitudinal motion of the drive stage housing moves in synchronization with the lead screw to maintain a firm contact of the head with the screw or drill bit as the screw or drill bit is rotatably driven into bone during a surgical procedure. In the embodiment where the inventive instrument drives a screw into bone, the instrument rotatably drives a surgical screw into bone, and the lead screw may have the same thread pitch as the surgical screw.

A rotational power source can be an electric or pneumatic motor, or the proximal end of the drive shaft may include a handle that is manually rotated by a surgeon to cause the drive shaft to rotate. A second handle may be provided on the shaft such that the surgeon can grip the instrument with two hands. In an embodiment, the rotational force (i.e., the torque) is redirected to an angle of 125° or 135° from the axis of the drive shaft. In an embodiment, the instrument rotatably drives a drill bit into bone during a surgical procedure, or rotatably drives a screw that secures an implant into bone, or rotatably drives a screw that secures an implant into spinal vertebrae.

DETAILED DESCRIPTION

As used herein the term "instrument" and "device" have the same meaning and are interchangeable. The terms "proximal" and "distal" as used herein are in relation to a surgeon working with the inventive instrument. For example, in FIG. 1A, the handle 130 is proximal, and gear housing 200 is distal. The terms "torque" and "rotational force" are interchangeable. The term "approximately," with respect to geometric angles, means ±3°.

A representative embodiment of the instant invention is shown in the figures. In an embodiment, this invention provides an instrument 100 for rotatably driving a screw (for example, 310) or drill bit (314) into bone in surgery, comprising a gear housing (200) at a distal end of a drive shaft (110), wherein the drive shaft has a proximal end adapted for connection to a rotational power source (for example, handle 130), wherein the gear housing comprises at least one pair of bevel gears (210, 212) that direct the rotational force from the drive shaft in an approximately 115°-145° (FIG. 1A, angle 320) angle from the drive shaft 110 to rotatably drive a screw or drill bit into bone during a surgical procedure. A preferential angle is approximately 135°. The inventive instrument provides a surgeon or user the ability to place a drill or screw at a fixed angle in a smaller surgical field and in a more user-friendly and natural position.

Figure 1A:
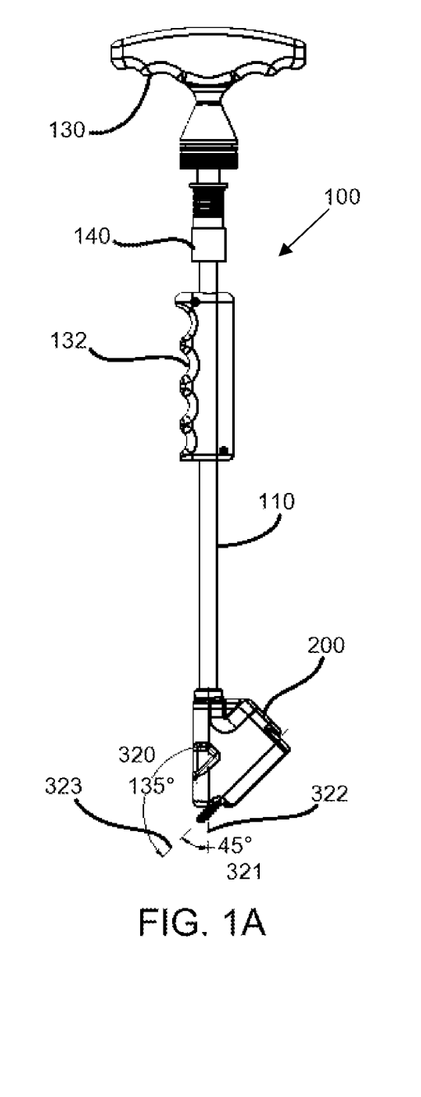
FIG. 1A is an elevation view of an embodiment of the inventive device with a handle for manual drive showing exemplary angles of redirected torque.
Figure 1B:
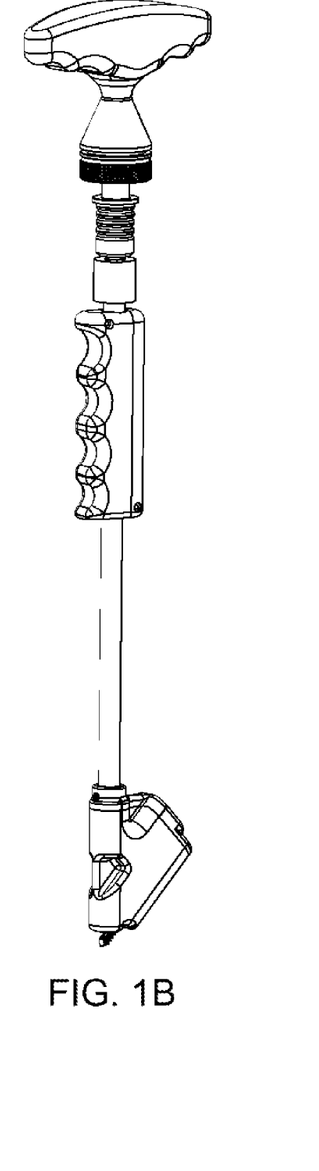
FIGS. 1B and 1C are isometric views of two different faces of an embodiment of the inventive device with a handle for manual drive.
Figure 1C:
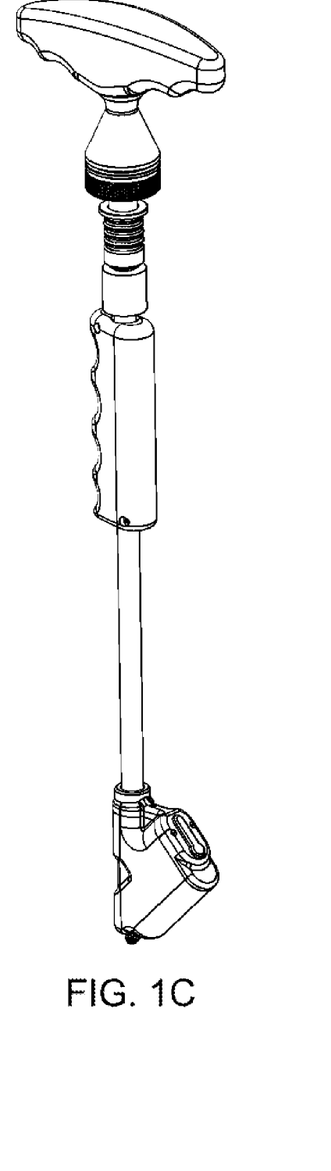
Figure 2:
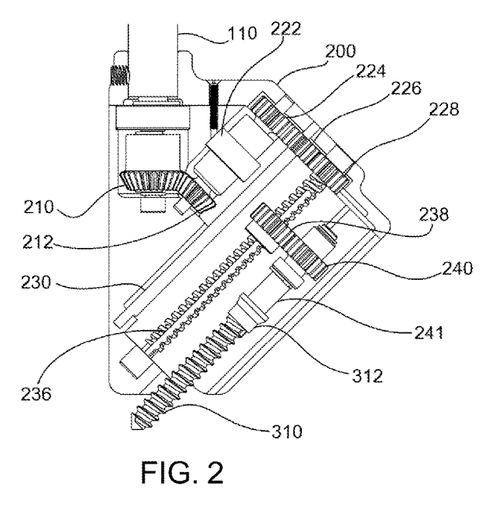
FIG. 2 is a cutaway plan view of an embodiment of the gear housing of the inventive instrument, with the drive stage housing omitted.
Figure 3:
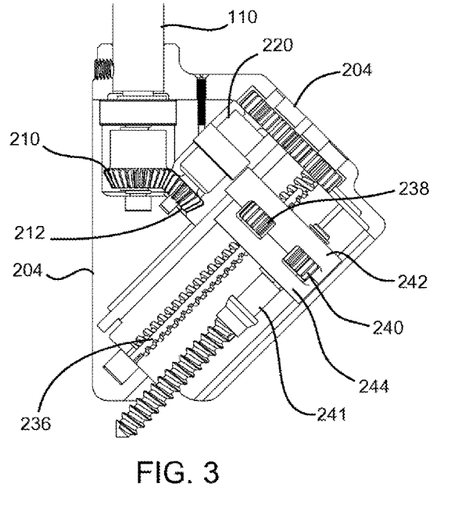
FIG. 3 is a cutaway plan view of an embodiment of the gear housing of the inventive instrument showing the drive stage housing.
Figure 4A:
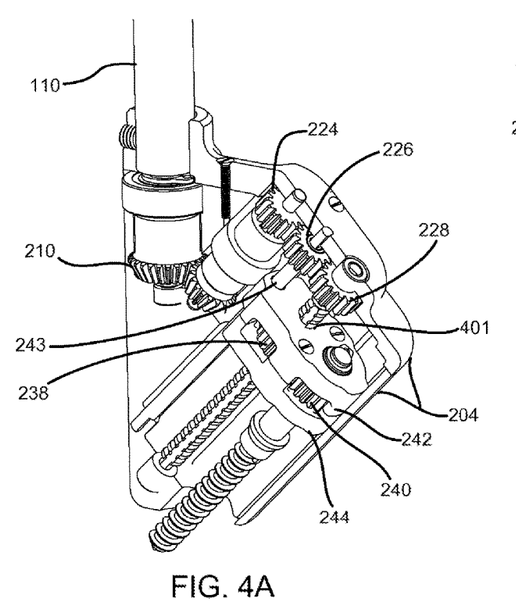
FIGS. 4A and 4B are isometric cutaway views from different angles of an embodiment of the inventive instrument showing the gearing in the gear housing.
Figure 4B:
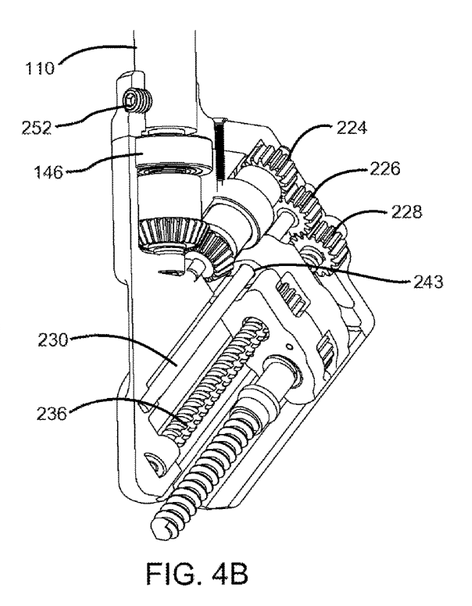

As shown in FIG. 1A, the angle between axis 322, an axis through the drive shaft, and axis 323, an axis through a screw for driving into bone, is angle 320 which is 135°. Angle 321, the difference between 180° and angle 320, is also an important angle for the internal gearing of the inventive device. FIG. 1A shows exemplary angles of 135° for 320 and 45° for angle 321, but as disclosed herein, angle 320 can be approximately 115°-145° and angle 321 may be approximately 35°-55°. The sum of angles 320+321 is 180°.

As shown in FIG. 1, the rotational power source is a handle 130 connected to drive shaft 110. However, other rotational power sources can be used, for example a electric motor or a pneumatic motor. Some examples are the Stryker® "System 8 Cordless Driver™," and the Ruijin® "ND-1011 Dual Functional Electric Orthopedic Bone Drill."[2]

[2] https://www.stryker.com/us/en/orthopaedic-instruments/products/system-8-cordless-driver-and-sabo.html, checked Feb. 20, 2021; https://www.orthopedicdrills.com/product/nd-1011-dual-functional-electric-bone-drill, checked Feb. 20, 2021

Also shown in FIG. 1 is a handle 132 with the drive shaft passing therethrough that gives the surgeon more precise control over handling and maneuvering the inventive instrument. In conjunction with handle 130, the surgeon will have a firm grip on the device with both hands.

In an embodiment, an instrument is provided for rotatably driving a screw (for example, 310) or drill bit (314) into bone in surgery. The instrument may include a drive shaft (110) having a rotational power source at a proximal end for applying a rotational force to the shaft and a gear housing (200) at a distal end 114 of the drive shaft. The distal end of the drive shaft may be connected to a first bevel gear (210) supported in the gear housing, such that the larger diameter of the first bevel gear is in the proximal orientation (that is, the proximal face of the bevel gear), such that rotation of the drive shaft causes the first bevel gear to rotate. The first bevel gear may mesh with a second bevel gear (212) having an axis at a 25°-55° angle to direct a torque from the second bevel gear at the 25°-55° angle along a first internal shaft (220), wherein the internal shaft terminates at a first spur gear (224) which in turn meshes with a second spur gear (for example 228), wherein the second spur gear drives a second internal shaft (for example, screw 236) that is coupled to a head (240) that rotatably drives a surgical screw (310) or drill at a 115°-145° angle from the drive shaft. The rotational power source may be an electric or pneumatic motor. Alternatively, the proximal end of the drive shaft may include a handle that is manually rotated by a surgeon to cause the drive shaft to rotate.

In an embodiment, an instrument 100 is provided for rotatably driving a screw (for example 310) or drill bit (314) into bone in surgery as shown in the figures. The instrument may include a drive shaft (110) having a rotational power source (for example, handle 130) at a proximal end for applying a rotational force to the shaft and a gear housing at a distal end of the drive shaft. The distal end of the drive shaft 110 may be connected to a first bevel gear (210) supported in the gear housing 200, such that the larger diameter of the first bevel gear is in the proximal orientation, such that rotation of the handle causes the first bevel gear to rotate. The first bevel gear may mesh with a second bevel gear (212) having an axis at a 25°-55° angle to direct a torque from the second bevel gear at the 25°-55° angle along a first internal shaft (220), wherein the internal shaft terminates at a first spur gear (224). The first spur gear meshes with at least one additional second spur gear (gears 226 and 228 in FIG. 4 and FIG. 5), wherein rotation of the at least one additional second spur gear causes a lead screw (236) to rotate. The first drive gear 238, which is linked to lead screw 236 with key 264, is driven by lead screw 236. Drive gear 238 rotates about lead screw 236 and translates along lead screw 236 via a key path (400), integral to lead screw 236, as rotational power is transmitted (see FIG. 7). Rotation of the first drive gear 238 causes the drive stage housing to move longitudinally along the lead screw, from a proximal position within pocket 208 to a distal position. A second spur drive gear (240) in the drive stage housing meshes with drive gear 238, such that rotation of drive gear 238 causes second drive gear 240 to rotate, and wherein drive gear 240 is connected to a head (stem 241) that rotatably drives a surgical screw (310) or drill bit (314) at a 115°-145° angle from the drive shaft, and wherein the longitudinal motion of the drive stage housing moves in synchronization with the lead screw to maintain a firm contact of the head with the screw or drill bit as the screw or drill bit is rotatably driven into bone during a surgical procedure. In the embodiment where the inventive instrument drives a screw into bone, the instrument rotatably drives a surgical screw into bone, and the lead screw may have the same thread pitch as the surgical screw.

The direction of rotation of the drive shaft can be reversed to cause the head 241 or socket 315 to retract. In this way, the surgeon can maintain precise control of the screwing or drilling operation. For example, if the drive shaft 110 has handle 130, the handle can be rotated in either direction to advance or retract the head 241 or drill bit socket 315.

Figure 7:
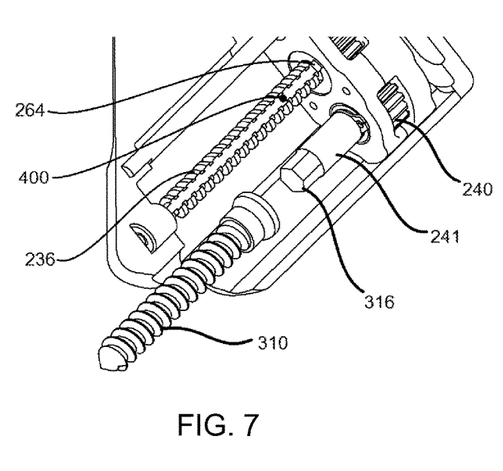
FIG. 7 is an isometric cutaway view of an embodiment of the inventive instrument showing a hex head screwdriver head for rotationally driving a screw.
Figure 8:
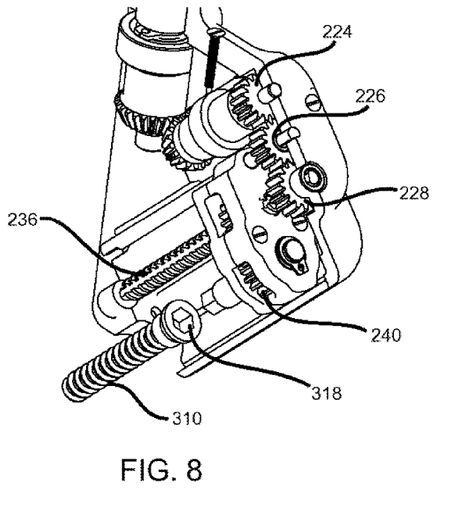
FIG. 8 is an isometric cutaway view of an embodiment of the inventive instrument showing a hex socket in the head of the screw.
Figure 9A:
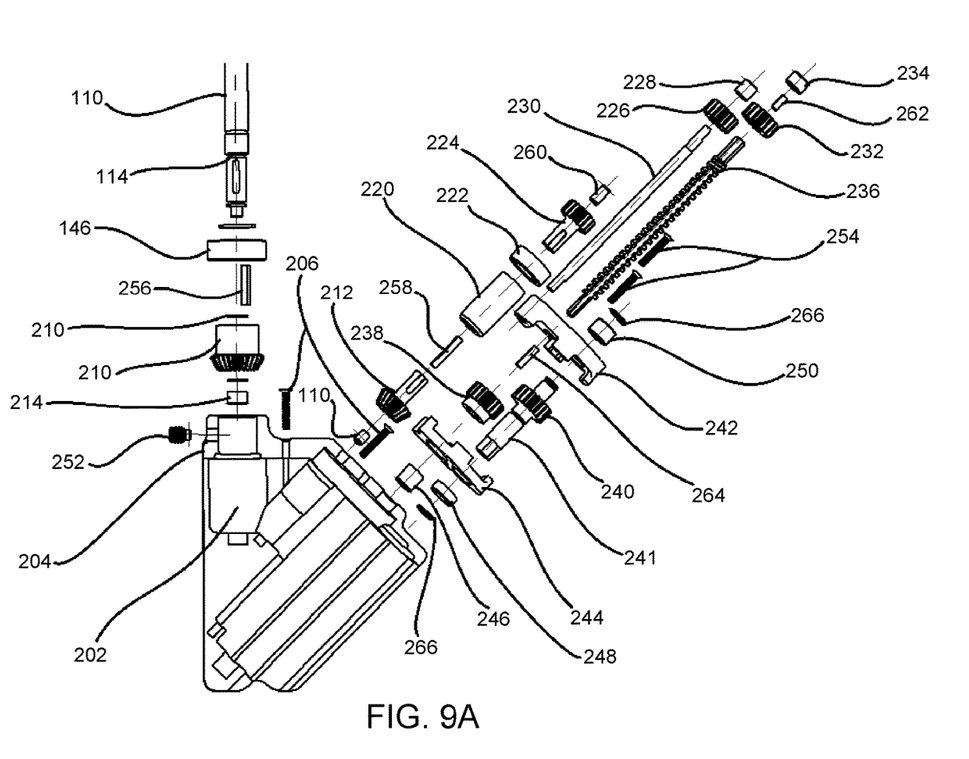
FIG. 9A is an exploded view of an embodiment of the inventive instrument.

A design embodiment of an instrument 100 for rotatably driving a screw or drill bit into bone in surgery in a fixed angle shown in various cutaway views in FIGS. 2-8. An exploded view showing all parts is FIGS. 9A and 9B. From the top left as depicted in FIG. 9A, drive shaft 110 is connected to shaft coupler 140 and sleeve bearing 142. Proximal end 112 of the drive shaft can be adapted to interface with any of several rotational power sources can be used, such as a handle 130 (FIG. 1) or a motor, for example an electric motor or a pneumatic motor. The distal end of drive shaft 110 terminates in bevel gear 210. Key 256 may be necessary for the linkage. Gear 210 is embedded in gear housing 200.

Figure 10:
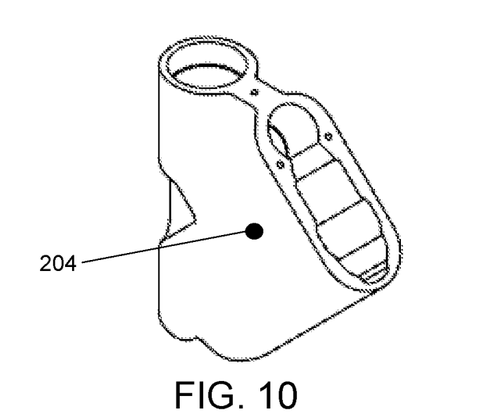
FIG. 10 is an isometric view of the exterior of the lower housing cover.
Figure 11:
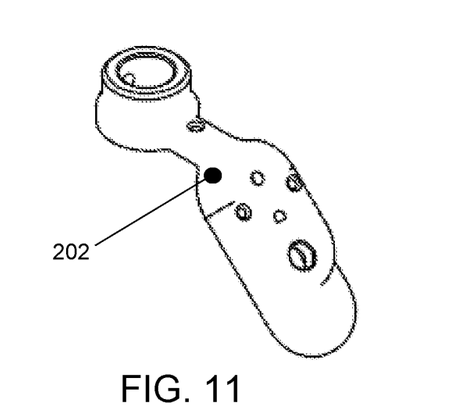
FIG. 11 is an isometric view of the exterior of the upper housing cover.

In an embodiment, there may be two covers to gear housing 200, upper housing cover 202 and lower housing casing 204. Casing 204 is also shown in FIG. 10. Cover 202 is shown in FIG. 11. All of the internal parts can be assembled into the lower housing and then the cover 202 can be screwed into position with screws 206.

Figure 9B:
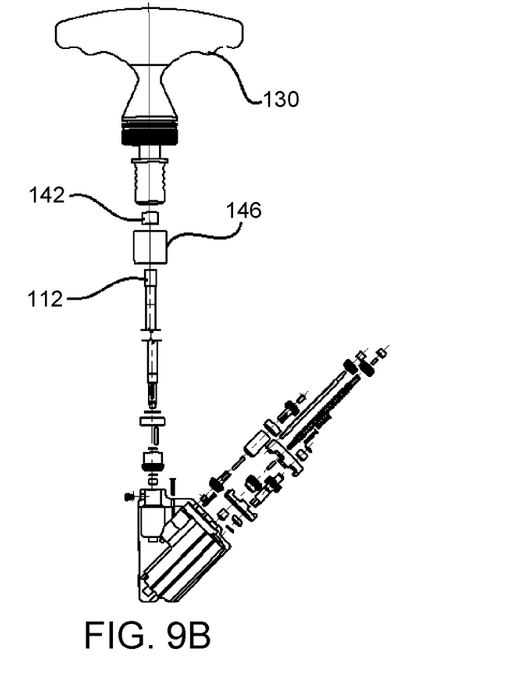
FIG. 9B is an exploded view of an embodiment of the inventive instrument showing a handle embodiment for driving the drive shaft.

As shown in FIGS. 2-8, bevel gear 210 meshes with second bevel gear 212. As shown in FIG. 9, there is a distal bearing 146 supporting the distal end of drive shaft 110 and the proximal end of bevel gear 210. A sleeve bearing 214 may be on the distal end of gear 210.

In an embodiment where the torque in the pair of bevel gears is directed at a 45° angle, as illustrated in FIGS. 2-8, each bevel gear will have a cone angle of 22.5°. Bevel gear 212 is connected to shaft coupler 220 with key 258 and is supported by sleeve bearing 222. The proximal end of the coupler 220 is connected to internal spur gear 224. As illustrated, spur gear 224 meshes with second spur gear 226, which in turn meshes with third spur gear 228. Internal spur gear 226 is supported by shaft 230, which extends from the upper housing over 202 to a distal position near the wall of lower housing 204. As discussed below, drive stage housing 242-244 slides on shaft 230 through aperture 243. Sleeve bearing 232 supports the proximal end of shaft 230. Sleeve bearing 234 supports the proximal end of lead screw 236 and spur gear 228. Dowel 260 supports spur gear 224.

Lead screw 236 is connected to internal spur gear 228, so that screw 236 rotates as gear 228 rotates. Upper drive stage housing 242 has aperture 401 (FIG. 4A), which is internally threaded for lead screw 236. Rotation of lead screw 236 causes drive stage housing 242/244 to move longitudinally along the axis of lead screw 236, i.e., the drive stage housing moves from a proximal to distal position. The drive stage housing is also supported by shaft 230. Shaft 230 penetrates drive stage housing 242/244 via aperture 243. Drive stage housing 242/244 also nests in pocket or cavity 208, that provides space for the drive stage housing to move longitudinally.

The rotation of spur gear 238 meshes with spur gear 240, and the rotation of 238 causes gear 240 to rotate. Gear 240 is also within drive stage housing 242/244. Stem 241, which may be integral with gear 240, terminates at the distal end in a head that can drive a screw, or interface with a drill bit.

Certain other parts shown in FIG. 9A include two screws 254 that join the upper drive stage housing 242 with lower drive stage housing 244. Also shown are sleeve bearings 246, 248, and 250 that provide necessary support for the gears in this embodiment.

Figure 12:
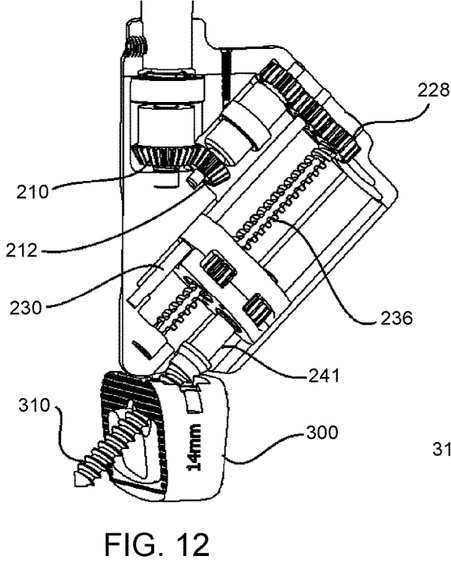
FIG. 12 is an isometric cutaway view of an embodiment of the inventive instrument showing an intervertebral cage and embedded screw insertable into bone.
Figure 13:
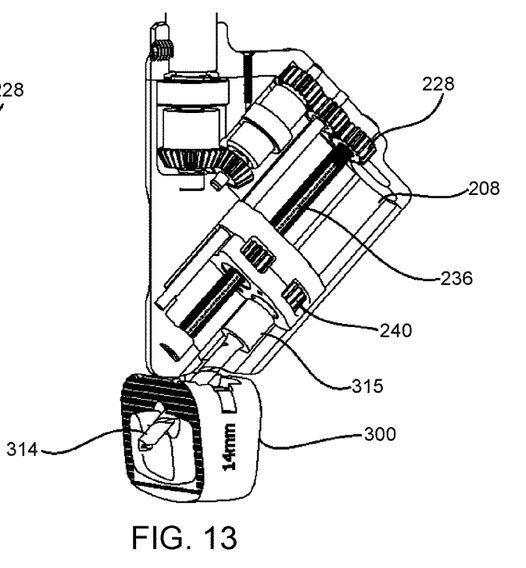
FIG. 13 is an isometric cutaway view of an embodiment of the inventive instrument showing an intervertebral cage and a drill bit insertable into bone.
Figure 14:
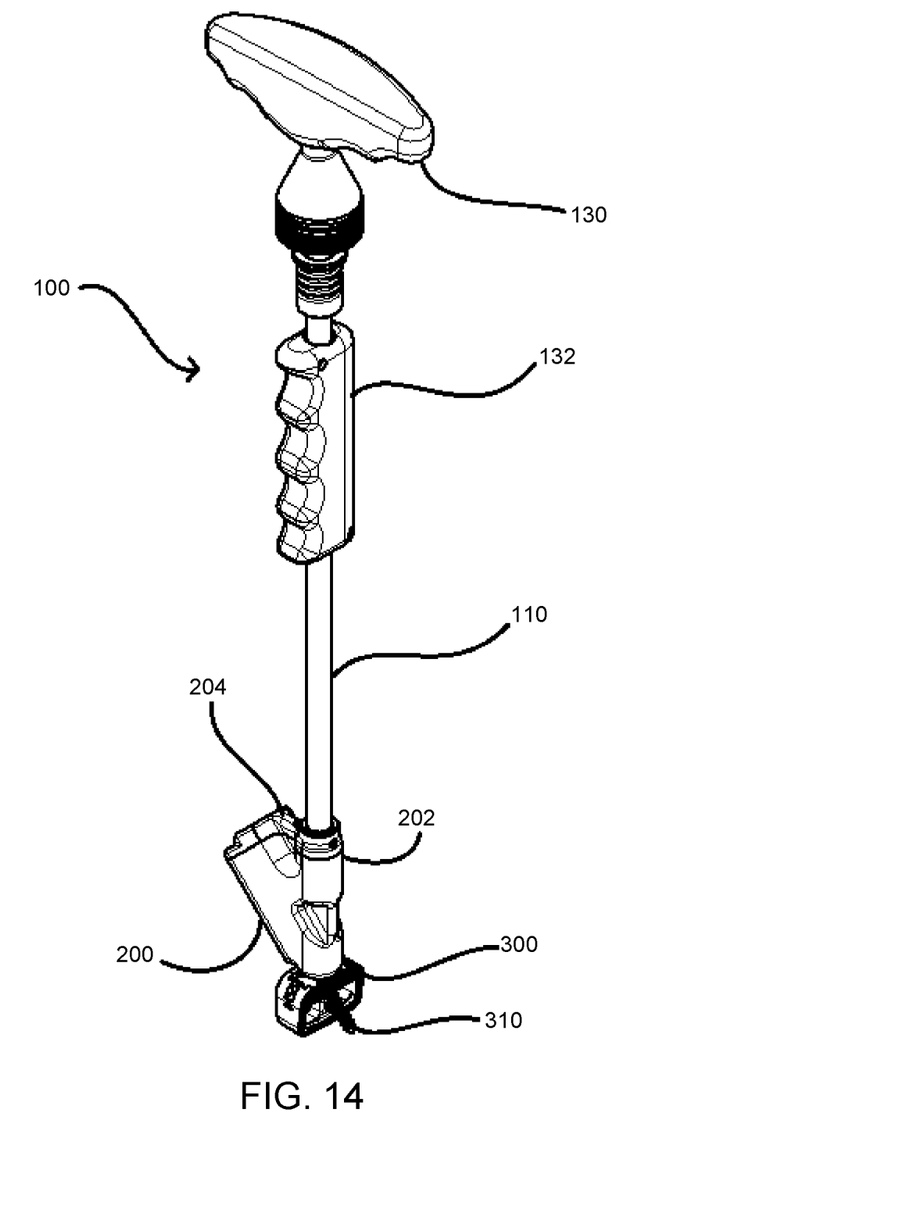
FIG. 14 is an isometric view of an embodiment of the inventive device with a handle for manual drive of an embodiment of the inventive device with a handle for manual drive showing an intervertebral cage and embedded screw insertable into bone.
Figure 15A:
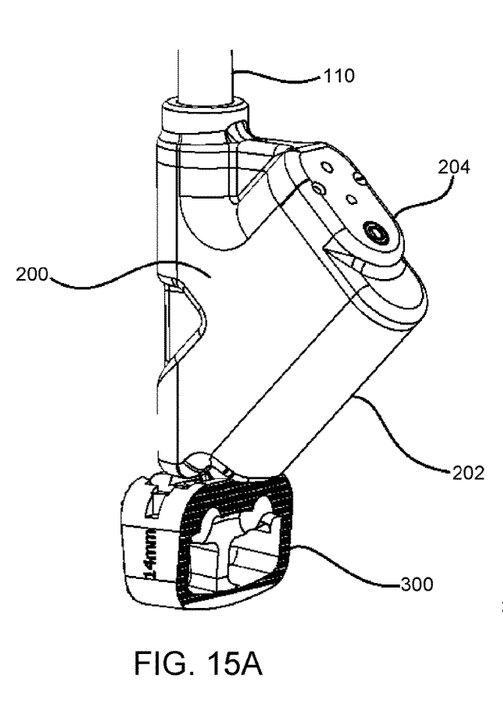
FIGS. 15A and 15B are two different isometric views from different angles of the exterior of the gear housing showing an intervertebral cage and embedded screw insertable into bone.
Figure 15B:
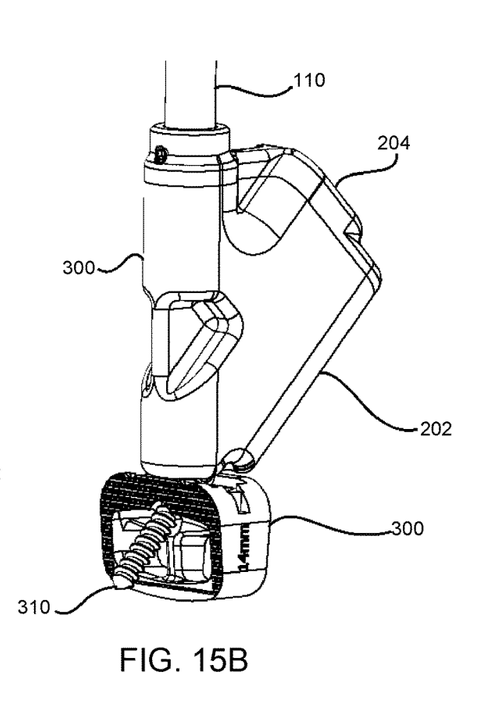

In an embodiment the pitch of lead screw 236 is the same pitch as surgical screw 310. Thus, if spur gears 238 and 240 are the same size, each 360° rotation of lead screw 236 will cause a 360° rotation of surgical screw 310. In this way, the head that is integral to stem 241 stays in consistent and steady contact with a socket in the head (312) of screw 310 adapted to accept a screwdriver head, such as a hex or torx socket. This coordinated rotation is less important if the inventive device is driving a drill bit. In an embodiment, the inventive device can be used to drive a screw included in an interbody fusion cage such as shim implant such as 300 or other implants or plates. These implants are often supplied with screws pre-threaded in the implant, as shown in FIG. 12. Such pre-threaded screws can be connected drive head 241 and rotationally screwed into position, with good control precision by the surgeon. FIG. 13 shows a drill bit through an implant 300. For example, after drilling a hole in this embodiment, a screw may be inserted. FIG. 14 is an isometric view of a complete embodiment of the inventive instrument 100 with shim cage implant 300 in place, ready for implantation. FIGS. 15A and 15B show an interbody fusion cage in exterior isometric views from different angles of the gear housing section 200 of the inventive implant.

Figure 5:
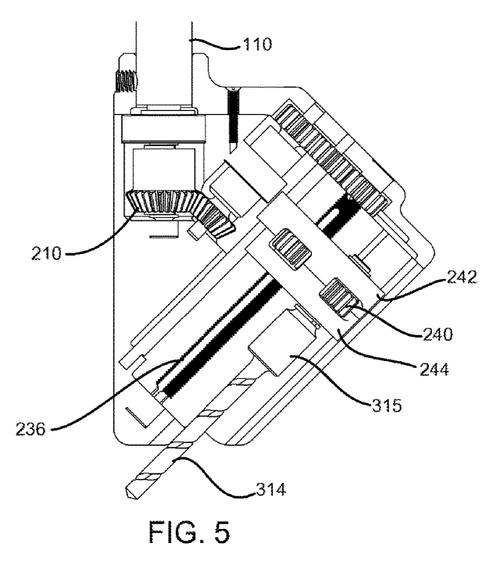
FIG. 5 is a cutaway plan view of an embodiment of the gear housing of the inventive instrument showing the drive stage housing with a drill bit embodiment.
Figure 6:
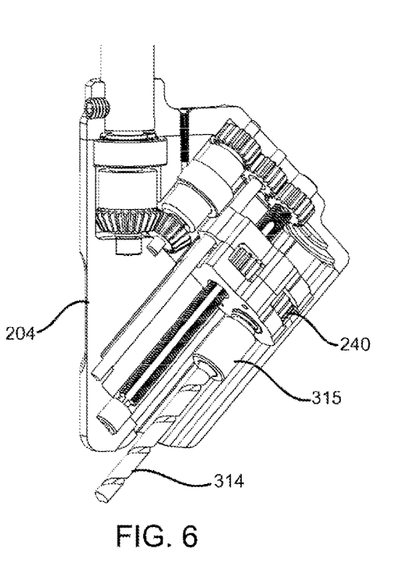
FIG. 6 is an isometric cutaway view of an embodiment of the inventive instrument showing the gearing in the gear housing and a drill bit.

In an embodiment, the inventive device may be adapted to drive a drill bit 314, shown in FIGS. 5 and 6. In an embodiment, the inventive devices are pre-configured to be used with a screw or drill bit. Several inventive devices may be configured with different size drill bits. An embodiment with a drill bit may employ a female socket 315 integral with spur gear 240 that rotational drives the drill bit into bone. An embodiment with a screw 310 is shown in FIGS. 7 and 8, showing details of an embodiment of a hex screwdriver head 316 integral with stem 241 and spur gear 240. FIG. 8 is a view of the hex socket 318 in the head of screw 310 for accepting the hex screwdriver head.

The inventive device may have no electronic parts and is washable and fully sterilizable at elevated temperature. The inventive devices may be fabricated from materials that can withstand washing and sterilization conditions.

Drawing Legend

| | |
|---|---|
| 100 | Exemplary instrument for rotatably driving a screw or drill bit into bone in surgery |
| 110 | Drive shaft |
| 112 | Proximal end of drive shaft |
| 114 | Distal end of drive shaft |
| 130 | Handle |
| 132 | Support handle |
| 140 | Shaft coupler |
| 142 | Sleeve bearing on shaft coupler 140 |
| 146 | Ball bearing supporting 110 |
| 200 | Gear housing |
| 202 | Upper housing cover |
| 204 | Lower housing casing |
| 206 | Screws (2) holding first and second housing cover |
| 208 | Pocket for movement of drive stage housing |
| 210 | First bevel gear |
| 212 | Second bevel gear |
| 214 | Sleeve bearing supporting 210 |
| 220 | Shaft coupler |
| 222 | Sleeve bearing supporting shaft coupler 220 |
| 224 | Internal spur gear 1 |
| 226 | Internal spur gear 2 |
| 228 | Internal spur gear 3 |
| 230 | Shaft supporting spur gear 2 |
| 232 | Sleeve bearing supporting spur gear 2 |
| 234 | Sleeve bearing supporting spur gear 3 |
| 236 | Lead screw |
| 238 | Drive spur gear 4 |
| 240 | Drive spur gear 5 |
| 241 | Stem of spur gear 6 |
| 242 | Drive stage housing upper |
| 243 | Aperture where shaft 230 penetrates 242/244 |
| 244 | Drive stage housing lower |
| 246 | Sleeve bearing supporting 238 |
| 248 | Sleeve bearing supporting 240 lower |
| 250 | Sleeve bearing supporting 240 upper |
| 252 | Set screw adjusting drive shaft |
| 254 | Screws joining drive stage housing upper and lower |
| 256 | Key linking drive shaft to first bevel gear |
| 258 | Key linking second bevel gear to internal spur gear 1 |
| 260 | Dowel pin supporting internal spur gear 1 |
| 262 | Key linking lead screw to spur gear 232 |
| 264 | Key linking drive gear 238 to lead screw 236 |
| 266 | Retaining ring (2) |
| 300 | Shim for distraction of vertebrae |
| 310 | Screw in shim or other screw for implantation into bone |
| 312 | Head of surgical screw |
| 314 | Drill bit |
| 315 | Socket for drill bit |
| 316 | Hex head screwdriver |
| 318 | Hex socket in surgical screw 310 |
| 320 | Angle of reorientation of torque |
| 321 | Angle of 180°- angle 320 |
| 322 | Axis of drive shaft |
| 323 | Axis of final drive |
| 400 | Key path integral to lead screw 236 |
| 401 | Drive stage housing aperture |

The invention claimed is:

1. An instrument for rotatably driving a screw or drill bit into bone in surgery, comprising
   a. a drive shaft having a rotational power source at a proximal end for applying a rotational force to the drive shaft and a gear housing at a distal end of the drive shaft;
   b. wherein the distal end of the drive shaft is connected to a first bevel gear supported in the gear housing, such that a larger diameter of the first bevel gear is in a proximal orientation, such that rotation of the drive shaft causes the first bevel gear to rotate;
   c. wherein the first bevel gear meshes with a second bevel gear having an axis of rotation at a 25°-55° angle to direct a torque from the second bevel gear at the 25°-55° angle along a first internal shaft, wherein the first internal shaft terminates at a first spur gear;
   d. wherein the first spur gear meshes with a second spur gear, wherein the second spur gear drives a second internal shaft that is coupled to a head that rotatably drives a surgical screw or drill at a 115°-145° angle from the drive shaft.

2. The instrument of claim 1, wherein the rotational power source is an electric or pneumatic motor.

3. The instrument of claim 1, wherein the proximal end of the drive shaft comprises a handle that is manually rotated by a surgeon to cause the drive shaft to rotate.

4. An instrument for rotatably driving a screw or drill bit into bone in surgery, comprising:
   a. a drive shaft having a rotational power source at a proximal end for applying a rotational force to the drive shaft and a gear housing at a distal end of the drive shaft;
   b. wherein the distal end of the drive shaft is connected to a first bevel gear supported in the gear housing, such that a larger diameter of the first bevel gear is in a proximal orientation, such that rotation of the drive shaft causes the first bevel gear to rotate;

c. wherein the first bevel gear meshes with a second bevel gear having an axis of rotation at a 25°-55° angle with respect to the drive shaft to direct a torque from the second bevel gear at the 25°-55° angle along a first internal shaft, wherein the first internal shaft terminates at a first spur gear;

d. wherein the first spur gear meshes with at least one additional second spur gear, wherein rotation of the at least one additional second spur gear causes a lead screw to rotate;

e. wherein the lead screw meshes with a drive stage housing containing a first drive gear, such that rotation of the lead screw causes the first drive gear to rotate, and wherein rotation of the first drive gear causes the drive stage housing to move longitudinally along the lead screw;

f. wherein a second drive gear in the drive stage housing meshes with the first drive gear, such that rotation of the first drive gear causes the second drive gear to rotate, and wherein the second drive gear is connected to a head that rotatably drives a surgical screw or drill bit at a 115°-145° angle from the drive shaft, and wherein the longitudinal motion of the drive stage housing moves in synchronization with the lead screw to maintain a firm contact of the head with the screw or drill bit as the screw or drill bit is rotatably driven into bone during a surgical procedure.

5. The instrument of claim 4, wherein the rotational power source is an electric or pneumatic motor.

6. The instrument of claim 4, wherein the proximal end of the drive shaft comprises a handle that is manually rotated by a surgeon to cause the drive shaft to rotate.

7. The instrument of claim 4, wherein the proximal end of the drive shaft comprises a handle that is manually rotated by a surgeon to cause the drive shaft to rotate and further comprising a second handle on the drive shaft such that the surgeon can grip the instrument with two hands.

8. The instrument of claim 4, wherein the instrument rotatably drives a surgical screw into bone, and wherein the lead screw has the same thread pitch as the surgical screw.

* * * * *